United States Patent [19]

Raynor et al.

[11] Patent Number: 5,176,844
[45] Date of Patent: Jan. 5, 1993

[54] ALKALI METAL N-HALO-ALKANESULFONAMIDES BLEACHING AGENTS

[75] Inventors: Robert J. Raynor, North Branford; Ralph S. Webber, Cheshire, both of Conn.

[73] Assignee: Olin Corporation, Cheshire, Conn.

[21] Appl. No.: 546,967

[22] Filed: Jul. 2, 1990

[51] Int. Cl.$^5$ ............................................. C01B 11/06
[52] U.S. Cl. ............................ 252/187.1; 252/187.33; 8/109
[58] Field of Search ......................... 252/187.33, 187.1

[56] References Cited

U.S. PATENT DOCUMENTS

| | | | |
|---|---|---|---|
| 2,427,097 | 9/1947 | Kamler et al. | 8/127.6 |
| 2,980,488 | 4/1961 | Kokorudz | 8/108 |
| 3,707,554 | 12/1972 | Hardy | 252/187.33 |
| 3,767,586 | 10/1973 | Rutkiewic | 252/187.33 |
| 3,829,385 | 8/1974 | Abbott, Jr. et al. | 252/95 |
| 3,850,920 | 11/1974 | Walles | 252/187.33 |
| 4,148,742 | 4/1979 | Crutchfield et al. | 252/102 |
| 4,382,799 | 5/1983 | Davis et al. | 8/107 |
| 4,909,956 | 3/1990 | Webber | 252/187.34 |

OTHER PUBLICATIONS

"Bleaching Agent", Kirk Othmer Encyclopedia of Chemical Technology, 3rd Edition, vol. 3, p. 947, 1978.

Primary Examiner—Richard D. Lovering
Assistant Examiner—Joseph D. Anthony
Attorney, Agent, or Firm—Donald M. Papuga; F. A. Iskander

[57] ABSTRACT

Described herein is the use of N-halo-alkene-sulfonamides as bleaching agents to remove stains from non-white stained materials.

7 Claims, No Drawings

ALKALI METAL N-HALO-ALKANESULFONAMIDES BLEACHING AGENTS

BACKGROUND OF THE INVENTION

1. Field of The Invention

This invention is directed to the use of alkali metal N-halo-alkanesulfonamides as bleaching agents for removing stains from non-white stained materials.

2. Brief Description of the Prior Art

Many bleaches which efficiently and effectively remove stains from non-white goods such as fabrics, most often damage the color by attacking the dyes used in these goods.

U.S. Pat. No. 3,707,554 describes alkali metal N-halo-alkanesulfonamides having bleaching and antiseptic properties and capable of being formulated in bleaching and detergent compositions and represented by the following formula:

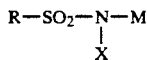

wherein X is chlorine or bromine, M is an alkali metal, and R is an alkyl having from 1 to about 22 carbon atoms. These compounds are prepared by reacting an alkanesulfonamide with an alkali metal hypochlorite or hypobromite. The patent additionally states that the compounds may be prepared by reacting an alkanesulfonamide with an alkali metal hydroxide and hypochlorous or hypobromous acid and the resulting alkali metal N-halo-alkanesulfonamide thereafter recovered.

The patent also states that the N-halo compounds are especially suitable for use in granular detergent compositions, in particular in heavy duty granular detergent compositions. In column 6 of the patent, a formulation is set forth containing the N-halo compound. The patent then states that the product is suitable for washing soiled white goods, e.g., table linen and bed linen at normal washing machine temperatures. This patent does not disclose the use of the alkali metal N-halo-alkanesulfonamides to remove stains from non-white materials.

BRIEF SUMMARY OF THE INVENTION

The present invention is directed to the use of alkali metal N-halo-alkanesulfonamides as bleaching agents for non-white goods, particularly fabrics. It has been found that the alkali metal N-halo-alkanesulfonamides remove stains from non-white materials, particularly fabrics without affecting the color of the materials.

DESCRIPTION OF THE PREFERRED EMBODIMENTS

In the present invention, alkali metal N-halo-alkanesulfonamides are used as bleaching agents to remove stains from non-white materials.

The alkali metal N-halo-alkanesulfonamides can be used as bleaching agents for non-white materials such as fabrics and cloths which can be made into a variety of end uses. The alkali metal N-halo-alkanesulfonamides are of the following formula:

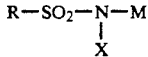

wherein R is an alkyl of 1 to about 25 carbon atoms, preferably from 10 to 25 carbon atoms, M is an alkali metal, preferably sodium and potassium and X is chlorine or bromine.

The non-white materials are treated with the alkali metal N-halo-alkanesulfonamide for a time and at a temperature sufficient to remove any stains therefrom. This is generally at a temperature of from about 5 to about 80 °C. and for a period of time sufficient to remove any stains.

The alkali metal N-halo-alkanesulfonamide may be prepared by any of the methods set forth in U.S. Pat. No. 3,707,554, discussed above.

Preferably, the N-halo compounds are prepared by reacting the alkanesulfonamide and one equivalent of alkali metal hydroxide and then adding one equivalent of a substantially pure sodium hypochlorite and thereafter recovering the resulting alkali metal N-halo-alkanesulfonamide. The substantially pure sodium hypochlorite is made from sodium hydroxide and the substantially pure hypochlorous acid prepared as described below. The reaction temperature is generally from about 25° to about 100° C.

The hypochlorous acid used in the instant process may be characterized as a solution containing greater than 5% by weight of hypochlorous acid, preferably from about 25 to about 60%, and most preferably from about 30 to about 50% by weight of hypochlorous acid. The hypochlorous acid solution is substantially free of chloride, chlorate, and alkali metal ions.

The concentrated hypochlorous acid solution may be produced from a gaseous mixture comprised of chlorine monoxide, hypochlorous acid vapor, chlorine, and water vapor, which process comprises condensing the gaseous mixture at a temperature in the range of from about −5° C. to about +10° C.

In more detail, the process for producing the concentrated hypochlorous acid solution comprises reacting an aqueous alkali metal hydroxide, such as sodium hydroxide, potassium hydroxide, or lithium hydroxide in droplet form with chlorine gas. The reaction is conducted at temperatures sufficiently high enough to vaporize hypochlorous acid as it is produced and separate it from solid particles of alkali metal chloride which are also formed in the reaction. As gaseous mixtures having high concentrations of hypochlorous acid and chlorine monoxide are desired, highly concentrated aqueous solutions of the alkali metal hydroxide are used. Suitable concentrations include those in the range of from about 40 to about 80%, and preferably from about 45 to about 60% by weight of alkali metal hydroxide. A stoichiometric excess of chlorine above that required to form hypochlorous acid with all of the alkali metal hydroxide is used, for example from about 1 to about 20, and preferably from about 5 to about 10 times the stoichiometric proportion of chlorine is employed. Solid particles of alkali metal chloride are also produced during the reaction which have a wide range of particles sizes.

The gaseous mixture comprised of hypochlorous acid vapor, chlorine monoxide, chlorine, and water vapor used in the process contains high concentrations of HOCl and $Cl_2O$. The chlorine monoxide is formed by the conversion of HOCl vapors during the vaporization process according to the equation:

$$2HOCl \rightleftharpoons Cl_2O + H_2O \qquad (1)$$

The gaseous mixture also contains fine particles of the alkali metal chloride which are entrained. The solid particles may be removed by any suitable separation means, for example, by passing the gaseous mixture through a gas filter medium or through a solid separator such as a cyclone.

The gaseous mixture, now free of solids, is fed to a condenser. The condenser is operated at temperatures which produce concentrated aqueous solutions of hypochlorous acid without condensing undesirable amounts of chlorine or liquid chlorine monoxide. Suitable temperatures for operating the condensation process include those in the range of from about $-5°$ C. to about $+20°$ C.

The uncondensed gaseous mixture recovered from the condenser is substantially anhydrous as the water vapor originally present was condensed to form the aqueous hypochlorous acid solution. While the hypochlorous acid concentration is significantly reduced, the chlorine gas concentration is substantially the same as that in the original gaseous mixture fed to the condenser.

The concentrated hypochlorous acid solution is highly pure. The dissolved chlorine concentration in the hypochlorous acid solution of the present invention is less than about 2% by weight. The concentrated hypochlorous acid solution is essentially free of ionic impurities such as alkali metal, chloride, and chlorate ions. Concentrations of the chloride ion are less than about 50 parts per million; the alkali metal ion concentration is less than about 50 parts per million; and the chlorate ion concentration is no more than about 100 parts per million.

A process for producing hypochlorous acid is described in, for example, U.S. Pat. No. 4,146,578, incorporated in its entirety herein by reference.

The alkali metal N-halo-alkanesulfonamides of this invention may be combined with other materials to be formulated into detergents and the like.

EXAMPLES

The following examples illustrate the process of this invention and are presented without the intention of being limited thereby:

Preparation of Hypochlorous Acid Solution

The following represents a typical process for the preparation of a concentrated hypochlorous acid solution useful in this invention:

A gaseous mixture containing an average concentration of 180.7 parts by weight of chlorine monoxide, 384.5 parts by weight of $Cl_2$, and 60.3 parts by weight of water vapor was continuously passed through a cyclone separator to remove any entrained solid particles of alkali metal chloride. The solid-free gaseous mixture at a temperature of 85-90° C. was passed through a vertical shell and tube heat exchanger maintained at a temperature of about 0° C. and a pressure of about 3-4 torr gauge to condense a portion of the chlorine monoxide and substantially all of the water vapor to produce an aqueous hypochlorous acid solution containing 45 to 50% by weight of HOCl. The hypochlorous acid solution had a pH of about 1 and the dissolved chlorine concentration was determined to be about 1% by weight. An uncondensed gas mixture containing an average of 141.9 parts by weight of $Cl_2O$, 384.1 parts by weight of $Cl_2$ and 0.5 parts by weight of water was continuously removed from the condenser. The uncondensed gas mixture was passed through a heat exchanger to raise the temperature to about 100° C. and recycled to a generator used to produce the gaseous mixture of chlorine monoxide.

Preparation of N-Chloro-N-Sodiododecanesulfonamide

A mixture of 12.0 grams (0.048 m) dodecylsulfonamide and 48 ml of a 1.0 N aqueous solution (0.048 m) of NaOH were stirred and heated at 90-100° C. for four minutes, then cooled to 50° C. To this solution was added at 50° C. and over a 30 sec. period 120 ml of a 3% aqueous solution (0.048 m) of sodium hypochlorite. This clear solution was stirred for 10 mins. at 50° C., then allowed to cool slowly to 25° C. without stirring. The crystals which formed on cooling were removed by filtration and recrystallized from 0.1 N NaOH to give 13 g. of the product N-chloro-N-sodiododecanesulfonamide.

EXAMPLES 1 to 4

The dye attack test was conducted as stated in the following method with one exception. The same N-chloro-N-sodiododecanesulfonamide/commercial high phosphate detergent was blended 4 parts detergent to 1 part bleach. The N-chloro-N-sodiododecanesulfonamide containing samples show only minor changes in reflectance (no dye attack) compared to dry chlorine bleach.

Fabric Pretreatment

1. Wash fabric in household clothes washer in warm water using one cup commercial high phosphate detergent or equivalent.
2. Cut fabric into 6"×6" swatches.
3. Measure color using Hunter ColorQuest Spectrophotometer or equivalent measure CIE L*a*b* scale using D65 illumenent and 10° observer angle (measure color with and without the Presence of UV light).

Test Procedure

1. Weigh 1 gram available chlorine equivalent of bleach. For example, a 50% blend of CDB ® Clearon contains 28% available chlorine. 1 gram available chlorine equivalent of the bleach would be 1/.28=3.57 grams of bleach.
2. Place bleach in the center of one swatch (dye side up) and mark as bottom. Smooth bound of bleach into approximate 2" circle.
3. Place second swatch (dye side down) on top of first swatch and bleach sample fold corners upward and over forming a pouch. Mark second swatch as top.
4. Dissolve 3 grams of detergent in 600 ml of 40° C. water.
5. Place bleach pouch in detergent solution with first swatch against the bottom of the beaker. Weigh pouch down with spatula.
6. Time for 90 seconds and remove swatch from detergent solution. Rinse off excess bleach and allow to air dry. Dispose of detergent-bleach solution.
7. After swatch(s) are dry, iron and measure color change using Hunter ColorQuest Spectrophotometer or equivalent. Measure CIE L*a*b* scale using D65 illumenent and 10° observer angle (measure with and without UV light).

In Table 1, the results demonstrate that in cold water the N-chlor-N-sodiododecanesulfonamide bleach removed 80–90% of tea stain applied to 100% cotton fabric. As a comparison detergent alone removes about 20% and CDB ® Clearon about 100%.

In Table 2, N-chlor-N-sodiododecanesulfonamide bleach was used in a denim dye attack test. No dye damage was noticed with either the bleach alone applied to the denim fabric or the block blended with the commercial high phosphate detergent then applied to the denim fabric. Chlorine dry bleach attacks the denim dye.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method of removing stains from non-white stained fabric which comprises contacting the stained fabric with at an aqueous composition comprising at least one alkali metal N-halo-alkanesulfonamide for a time and temperature sufficient to remove said stains, without adversely affecting dye color of said non-white fabric.

2. A method as defined in claim 1, which is carried out at a temperature of from about 5° to about 80° C.

3. A method as defined in claim 2, wherein the alkali metal N-halo-alkanesulfonamide is N-chloro-N-sodiododecanesulfonamide.

4. A method as defined in claim 1, wherein the alkali metal N-halo-alkanesulfonamide is of the following formula:

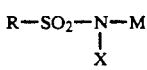

wherein R is alkyl of 1 to about 25 carbon atoms, M is an alkali metal, and X is chlorine or bromine.

5. A method as defined in claim 4, wherein R is alkyl of 10 to 25 carbon atoms.

6. A method as defined in claim 4, wherein M is sodium or potassium.

7. A method as defined in claim 5, wherein the N-halo-alkanesulfonamide is N-chloro-N-sodiododecanesulfonamide.

TABLE 1

Tea Stain Removal Testing
Conditions: Cold tap water; Terg-O-Tometer;
10 minute wash at 100 rpm; 2–5 min. rinses.

|  | CIE Value Average | | | Delta | | | |
| --- | --- | --- | --- | --- | --- | --- | --- |
|  | L | a | b | L | a | b | Stain Removal |
| Tea Stain | 89.83 | 0.58 | 10.43 |  |  |  |  |
| White Fabric | 96.20 | −1.08 | 1.48 | 6.37 | −1.66 | −8.95 |  |
| Detergent Only | 91.04 | −.58 | 6.44 | 1.21 | −1.16 | −3.99 | 19.0 |
| Sulfonamide[1] 50 ppm | 94.98 | −1.03 | 3.42 | 5.15 | −1.61 | −7.01 | 80.8 |
| Sulfonamide[1] 100 ppm | 95.53 | −1.15 | 2.63 | 5.70 | −1.73 | −7.80 | 89.5 |
| CDB ® Clearon[2] 50 ppm | 96.45 | −1.20 | 0.96 | 6.62 | −1.78 | −9.47 | 103.9 |
| CDB Clearon[2] 100 ppm | 96.40 | −1.17 | 0.94 | 6.57 | −1.75 | −9.49 | 103.1 |

Stain Removal = $\dfrac{L_{test} - L_{tea\ stain}}{L_{fabric} - L_{tea\ stain}}$

TABLE 2

Denim Dye Attack
Conditions: Cold tap water; 6" × 6" denim swatches-2 swatches face-to-face with sample between corners folded up to form pouch; 90 sec. immersion of pouch in water.

|  | CIE Value | | | Change In | | |
| --- | --- | --- | --- | --- | --- | --- |
| Sample | L | a | b | L | a | b |
| Denim | 20.98 | 1.19 | −9.46 |  |  |  |
| Chlorine Dry Bleach | 85.64 | 3.46 | 32.00 | 64.66 | 2.27 | 41.46 |
| Sulfonamide[1] | 21.32 | 0.75 | −11.56 | 0.44 | −.44 | −2.10 |
| Sulfonamide[1]/Detergent[3] | 1.32 | 0.75 | −11.56 | 0.55 | −.44 | −2.10 |

[1]Sulfonamide is N-Chloro-N-Sodiododecanesulfonamide
[2]CDB-Clearon is sodium dicholor-s-triazinetrione dihydrate, a commercial bleach available from Olin Corp.
[3]Sulfonamide[1] blended together with the commercial high phosphate detergent.